US00PP16041P2

(12) United States Plant Patent
Hoogendoorn

(10) Patent No.: US PP16,041 P2
(45) Date of Patent: Oct. 18, 2005

(54) ***ALSTROEMERIA* PLANT NAMED 'ZALSACREA'**

(50) Latin Name: *Alstroemeria hybrida*
Varietal Denomination: Zalsacrea

(75) Inventor: Cornelis Arie Hoogendoorn, Aarlanderveen (NL)

(73) Assignee: Van Zanten Plants B.V., Rijsenhout (NL)

( * ) Notice: Subject to any disclaimer, the term of this patent is extended or adjusted under 35 U.S.C. 154(b) by 54 days.

(21) Appl. No.: 10/945,180

(22) Filed: Sep. 20, 2004

(51) Int. Cl.[7] ..... A01H 5/00
(52) U.S. Cl. ..... Plt./309
(58) Field of Search ..... Plt./309

*Primary Examiner*—Kent Bell
(74) *Attorney, Agent, or Firm*—C. A. Whealy

(57) ABSTRACT

A new and distinct cultivar of *Alstroemeria* plant named 'Zalsacrea', characterized by its erect and strong flowering stems; vigorous growth habit; intense red-colored flowers; and good postproduction longevity.

1 Drawing Sheet

Botanical classification/cultivar designation: *Alstroemeria hybrida* cultivar Zalsacrea.

BACKGROUND OF THE INVENTION

The present Invention relates to a new and distinct cultivar of *Alstroemeria* plant, botanically known as *Alstroemeria hybrida*, commercially used as a cut flower *Alstroemeria*, and hereinafter referred to by the name 'Zalsacrea'.

The new *Alstroemeria* is a product of a planned breeding program conducted by the Inventor in Hillegom, The Netherlands. The objective of the breeding program was to develop new cut flower *Alstroemeria* cultivars with desirable flower and plant qualities, attractive flower colors and excellent postproduction longevity.

The new *Alstroemeria* originated from a cross-pollination made by the Inventor in June, 1998 in Hillegom, The Netherlands, of a proprietary *Alstroemeria hybrida* selection identified as 95124-001PN, not patented, as the female, or seed, parent with a proprietary *Alstroemeria hybrida* selection identified as 97132-014, not patented, as the male, or pollen, parent. The new *Alstroemeria* was discovered and selected by the Inventor as a flowering plant within the progeny of the stated cross-pollination in a controlled environment in Hillegom, The Netherlands in 1999.

Asexual reproduction of the new cultivar by root divisions in a controlled environment in Hillegom, The Netherlands, since August, 1999, has shown that the unique features of this new *Alstroemeria* are stable and reproduced true to type in successive generations of asexual propagation.

SUMMARY OF THE INVENTION

Plants of the cultivar Zalsacrea have not been observed under all possible environmental conditions. The phenotype may vary somewhat with variations in environment such as temperature and light intensity without, however, any variance in genotype.

The following traits have been repeatedly observed and are determined to be the unique characteristics of 'Zalsacrea'. These characteristics in combination distinguish 'Zalsacrea' as a new and distinct cultivar:

1. Erect and strong flowering stems.
2. Vigorous growth habit.

3. Intense red-colored flowers.
4. Good postproduction longevity.

Plants of the new *Alstroemeria* can be compared to plants of the female parent selection. In side-by-side comparisons conducted in Hillegom, The Netherlands, plants of the new *Alstroemeria* differed from plants of the female parent selection in the following characteristics:

1. Plants of the new *Alstroemeria* had larger flowers than plants of the female parent selection.
2. Plants of the new *Alstroemeria* and the female parent selection differed in flower color as plants of the female parent selection had soft purple-colored flowers.

Plants of the new *Alstroemeria* can be compared to plants of the male parent selection. In side-by-side comparisons conducted in Hillegom, The Netherlands, plants of the new *Alstroemeria* differed from plants of the male parent selection in the following characteristics:

1. Plants of the new *Alstroemeria* had shorter pedicels than plants of the male parent selection.
2. Plants of the new *Alstroemeria* and the male parent selection differed in flower color as plants of the male parent selection had yellow-colored flowers.

Plants of the new *Alstroemeria* can also be compared to plants of the cultivar Stadutia, disclosed in U.S. Plant Pat. No. 6,785. In side-by-side comparisons conducted in Hillegom, The Netherlands, plants of the new *Alstroemeria* differed from plants of the cultivar Stadutia in the following characteristics:

1. Plants of the new *Alstroemeria* were shorter than plants of the cultivar Stadutia.
2. Plants of the new *Alstroemeria* had darker red-colored flowers than plants of the cultivar Stadutia.

BRIEF DESCRIPTION OF THE PHOTOGRAPH

The accompanying colored photograph illustrates the overall appearance of the new *Alstroemeria*, showing the colors as true as it is reasonably possible to obtain in colored reproductions of this type. Colors in the photograph may differ slightly from the color values cited in the detailed botanical description which accurately describe the colors of the new *Alstroemeria*. The photograph comprises a side perspective view of a typical flowering stem of 'Zalsacrea'.

DETAILED BOTANICAL DESCRIPTION

The aforementioned photograph and following observations and measurements describe plants of the new *Alstroemeria* grown in Rijsenhout, The Netherlands in a glass-covered greenhouse in ground beds. During the production of the plants, day temperatures ranged from 15 to 25° C., night temperatures ranged from 10 to 15° C. and light levels averaged 5,000 lux. Plants used for the photograph and description were about one year-old. The photograph and the description were taken during August and September. Color references are made to The Royal Horticultural Society Colour Chart, 1995 Edition, except where general terms of ordinary dictionary significance are used.

Botanical classification: *Alstroemeria hybrida* cultivar Zalsacrea.

Parentage:

*Female parent.*—Proprietary *Alstroemeria hybrida* selection identified as 95124-001PN, not patented.

*Male parent.*—Proprietary selection of *Alstroemeria hybrida* identified as 97132-014, not patented.

Propagation:

*Type.*—By root divisions.

*Root description.*—Fibrous, fleshy, thick; white, close to 155D, in color.

*Rooting habit.*—Freely branching.

*Rhizomes.*—Shape: Elongate; rounded. Length: About 10 to 30 cm. Diameter: About 3 to 10 mm. Texture: Smooth. Color: Close to 155D.

Plant description:

*Plant habit.*—Upright; freely branching, bushy appearance. Vigorous growth habit.

*Time from planting to harvest of cut flowers.*—About 80 to 90 days.

*Number of flowering stems produced per year.*—About 200 to 240.

*Plant height.*—About 90 to 180 cm.

*Plant diameter* (*spread*).—About 20 to 30 cm.

*Flowering stem description.*—Aspect: Erect. Length: About 1.25 to 1.85 meters. Diameter: About 6 to 8 mm. Internode length: About 2 to 4 cm. Strength: Strong. Texture: Glabrous. Color: Close to 144A; glossy.

*Foliage description.*—Leaves asymmetrical; sessile. Length: About 14 to 17 cm. Width: About 2.5 to 4.5 cm. Shape: Linear to lanceolate. Apex: Acute. Base: Attenuate. Margin: Entire. Texture, upper and lower surfaces: Smooth, glabrous. Venation pattern: Parallel. Color: Developing and fully developed foliage, upper surface: Close to 137A to 137B; slightly glossy. Developing and fully developed foliage, lower surface: Close to 137C. Venation: Upper surface, close to 137A to 137B; lower surface, close to 137C.

Flower description:

*Flower type and habit.*—Single cup-shaped flowers arranged in compound umbels. Perianth segments separate. Freely and continuously flowering. Flowers not persistent.

*Natural flowering season.*—Flowering continuous during the spring in The Netherlands.

*Fragrance.*—None detected.

*Flower longevity on the plant.*—About four weeks.

*Flower longevity as a cut flower.*—About 12 to 16 days.

*Flower buds* (*showing color*).—Length: About 2.5 to 4.5 cm. Diameter: About 1 to 2 cm. Shape: Roughly ovoid. Color: Greenish yellow.

*Umbel height.*—About 10 to 12 cm.

*Umbel diameter.*—About 15 to 20 cm.

*Number of flowers per umbel.*—About 15 to 20.

*Flower length* (*height*).—About 5 to 7 cm.

*Flower diameter.*—About 4.5 to 6 cm.

*Flower depth.*—About 6 to 6.5 cm.

*Perianth.*—Arrangement: Six arranged in two whorls, each whorl with two lateral and one median segments. Size, inner perianth: Length, lateral segments: About 4.5 to 6.5 cm. Length, median segment: About 3.5 to 5 cm. Width, lateral segments: About 1.5 to 2 cm. Width, median segment: About 1 to 2 cm. Size, outer perianth: Length, lateral and median segments: About 4.5 to 6.5 cm. Length, median segment: About 4.5 to 6.5 cm. Width, lateral segments: About 3 to 4 cm. Width, median segment: About 3.5 to 4 cm. Shape, inner perianth, lateral and median segments: Oblanceolate. Shape, outer perianth, lateral and median segments: Obovate. Apex, inner perianth, lateral and median segments: Acute. Apex, outer perianth, lateral and median segments: Bracket-shaped. Base, inner and outer perianths, lateral and median segments: Attenuate. Margin, inner and outer perianths, lateral and median segments: Entire; weakly undulate. Texture, inner and outer perianths, lateral and median segments: Smooth, glabrous; velvety. Color, inner perianth: When opening and fully opened, lateral segments, upper surface: Towards the apex, 46A; mid-section, 3C; towards the base, 14B; stripes, purplish close to 187A; tip, whitish close to 155D. When opening and fully opened, median segment, upper surface: Close to 46A; stripes, purplish close to 187A; tip, whitish close to 155D. When opening and fully opened, lateral segments, lower surface: Towards the apex, 46A; mid-section, 3C; towards the base, 21A; stripes, purplish close to 187A; tip, whitish close to 155D. When opening and fully opened, median segment, lower surface: Close to 46A; tip, whitish close to 155D. Color, outer perianth: When opening and fully opened, lateral and median segments, upper surface: Close to 46A; few stripes, purplish close to 187A; apex, greenish. When opening and fully opened, lateral and median segments, lower surface: Close to 46A; apex and venation, greenish.

*Peduncles.*—Length: About 4 to 8 cm. Diameter: About 3 to 4 mm. Strength: Strong. Angle: About 20 to 50° from vertical. Texture: Smooth, glabrous. Color: Close to 146B.

*Pedicels.*—Length: About 1.5 to 2.5 cm. Diameter: About 2 to 4 mm. Strength: Strong. Angle: About 20 to 50° from vertical. Texture: Smooth, glabrous. Color: Close to 146B.

*Reproductive organs.*—Stamens: Quantity per flower: Six. Anther shape: Elliptical. Anther length: About 8 mm. Anther diameter: About 2 mm. Anther color: Close to 183B. Pollen amount: Scarce. Pollen color: Between 165A and 165B. Pistils: Quantity per flower: One. Style length: About 3.5 to 4.5 cm. Style color: Reddish. Stigma color: Purple. Ovary color: Close to 137C.

*Fruit.*—Shape: Globular. Color: Brownish.

Disease/pest resistance: Plants of the new *Alstroemeria* have not been observed to be resistant to pathogens and pests common to *Alstroemeria*.

Temperature tolerance: Plants of the new *Alstroemeria* have been observed to tolerate temperatures from −5 to 40° C.

It is claimed:

1. A new and distinct cultivar of *Alstroemeria* plant named 'Zalsacrea', as illustrated and described.

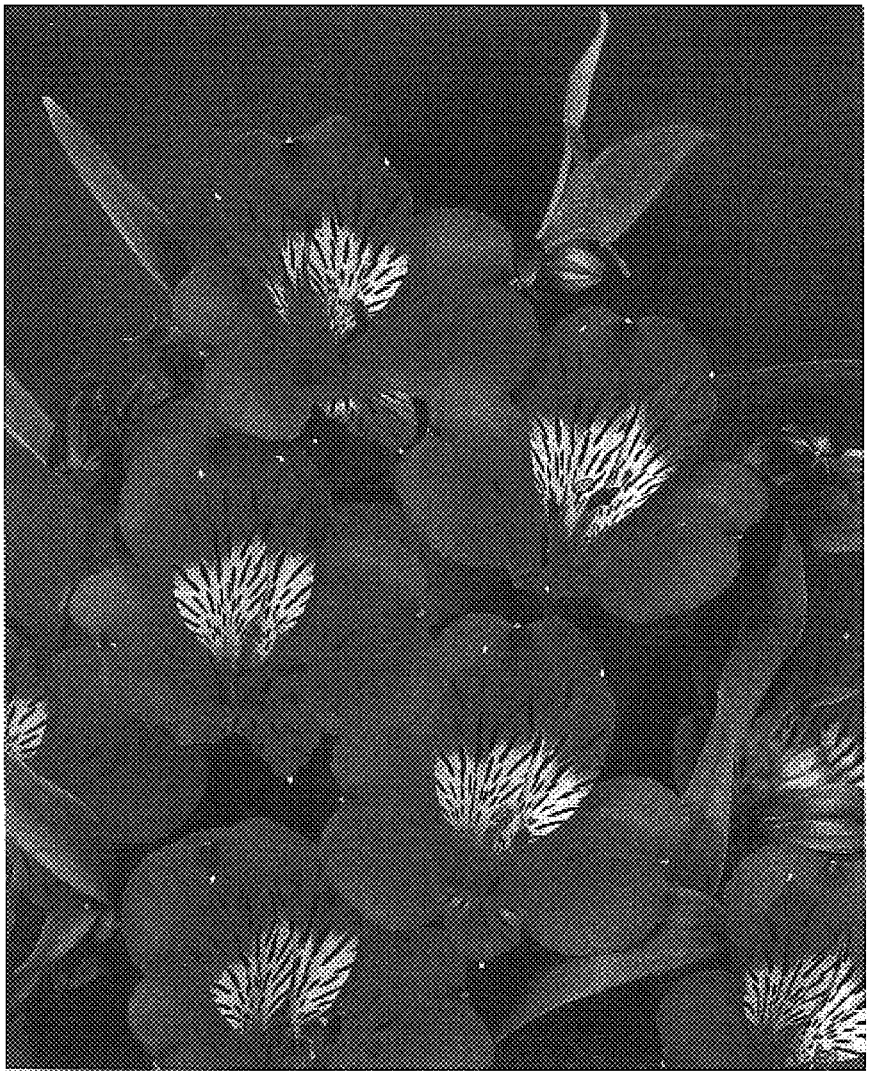

* * * * *